(12) United States Patent
Marsh

(10) Patent No.: US 9,060,897 B2
(45) Date of Patent: Jun. 23, 2015

(54) SWITCHABLE HEARING PROTECTION EAR PLUG

(71) Applicant: Robert E. Marsh, Kansas City, MO (US)

(72) Inventor: Robert E. Marsh, Kansas City, MO (US)

( * ) Notice: Subject to any disclaimer, the term of this patent is extended or adjusted under 35 U.S.C. 154(b) by 76 days.

(21) Appl. No.: 14/058,010

(22) Filed: Oct. 18, 2013

(65) Prior Publication Data

US 2015/0107606 A1   Apr. 23, 2015

(51) Int. Cl.
*A61F 11/00* (2006.01)
*A61F 11/08* (2006.01)

(52) U.S. Cl.
CPC ........... *A61F 11/08* (2013.01); *A61F 2011/085* (2013.01)

(58) Field of Classification Search
CPC .... A61F 11/08; A61F 2011/085; A61F 11/10

USPC .................................................. 128/848–868
See application file for complete search history.

(56) References Cited

U.S. PATENT DOCUMENTS

| | | | | | |
|---|---|---|---|---|---|
| 2,619,960 | A | * | 12/1952 | Reynolds ....................... | 128/868 |
| 2,717,596 | A | * | 9/1955 | Knight .......................... | 128/867 |
| 7,182,087 | B1 | * | 2/2007 | Marsh ........................... | 128/867 |
| 7,478,702 | B2 | * | 1/2009 | Berg et al. ..................... | 181/135 |
| 7,512,243 | B2 | * | 3/2009 | Haussmann .................... | 381/72 |
| 8,345,906 | B1 | * | 1/2013 | Kataw ............................ | 381/328 |

* cited by examiner

*Primary Examiner* — Kristen Matter

(57) ABSTRACT

The present invention is a switchable hearing protection ear plug. In one position, the ear plug provides substantial sound attenuation and hearing protection. In the second position, an opening in the ear plug permits sounds to enter the ear of the user relatively unobstructed. A deformable barrier in an interior chamber of the ear plug controls the passage of sound through the ear plug.

8 Claims, 1 Drawing Sheet

SWITCHABLE HEARING PROTECTION EAR PLUG

RELATED APPLICATIONS

This application claims the benefit of U.S. Provisional Patent Application No. 61/795,750, filed Oct. 24, 2012.

BACKGROUND OF THE INVENTION

The present invention generally relates to ear plugs for the protection of human hearing, and more particularly, to a hearing protection ear plug that can be easily switched between a position which provides substantial hearing protection and a second position that permits normal sound transmission.

Resilient foam ear plugs are widely used to provide hearing protection. A cylindrical foam earplug may be compressed and inserted into the ear canal, where it expands and conforms to the ear canal. In its expanded position, this foam earplug provides a high level of hearing protection. The "foam" used in these ear plugs (and as the term "foam" is broadly used in this application) can constitute one of many possible soft resilient materials, including silicone, neoprene, polyvinyl chloride, polyurethane, and others. Foam ear plugs are effective both as a result of the sound attenuation properties of the foam and the complete closure that results from expansion of the foam to contact the entire circumference of the ear canal. It is important for the effectiveness of this ear plug that it remains firmly positioned within the ear canal in its expanded configuration.

Hearing protection is needed in situations such as firearm shooting activities and industrial settings where there may be periods of loud noise followed by periods of no noise in which normal conversation is desirable. With prior art foam ear plugs, however, conversation is very difficult because of the high level of sound attenuation afforded by the ear plug. To permit more normal conversation the ear plug must be removed, then recompressed and reinserted into the ear canal before loud noises are again encountered. In any situation in which a user's hands may become dirty (such as in handling a firearm or in an industrial workplace setting) the recompression of the earplug for reinsertion into the ear can result in contamination of the surface of the earplug and transfer of that contamination to the ear canal of the user.

U.S. Pat. No. 7,182,087 describes a two position hearing protector that provides substantial sound attenuation and hearing protection in one position, and in a second position allows sounds to enter the ear of the user relatively unobstructed. That patent describes a mechanical switching mechanism for switching the ear plug from the open to closed position. The present invention is an improvement on the hearing protector of U.S. Pat. No. 7,182,087 and provides a novel and advantageous internal mechanism for switching between the sound attenuating and non-sound attenuating positions of the ear plug.

SUMMARY OF THE INVENTION

The present invention is a switchable hearing protection ear plug. In one position, the ear plug provides substantial sound attenuation and hearing protection. In the second position one or more openings in the ear plug permit sounds to enter the ear to the user relatively unobstructed. Sound passes through an interior chamber in the ear plug and a deformable barrier within the interior chamber either blocks the sound or allows sound to pass through the ear plug to the ear canal of the user.

It is an object of this invention to provide a hearing protection ear plug that can be easily switched from a position of substantial hearing protection and sound attenuation to a position of reduced sound attenuation which permits more normal hearing and conversation. A further object of this invention to provide a hearing protection ear plug that the user does not need to remove in order to carry on normal conversation. Still another object of the invention is to provide a compressible ear plug that conforms to the ear canal of the user but also permits convenient switching from a position providing substantial hearing protection and sound obstruction to a position of minimal sound obstruction. Still another object of the present invention is to permit switching between minimal and maximum sound attenuation positions while keeping the ear plug fully inserted in the ear canal.

DETAILED DESCRIPTION OF THE INVENTION

Figure 1:
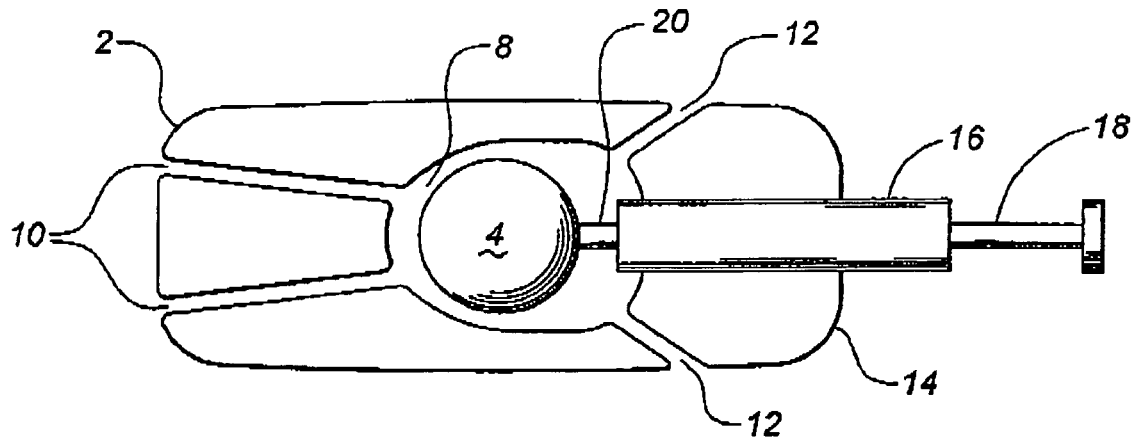
FIG. 1 shows a preferred embodiment of the hearing protection ear plug in the open position in which sounds are minimally attenuated.

FIG. 1 shows a preferred embodiment of the hearing protector ear plug 1. The exterior surface of the hearing protector ear plug is ideally made of a resilient foam or similar material. The foam should be easily compressible by hand and should return to its original dimensions (or exert pressure against the ear canal of the user) when released. As shown in FIG. 1, the foam ear plug has a base end 2 that is inserted into the ear of the user. A deformable barrier 4, in this case spherical in shape, is located within an interior chamber 8 in the ear plug. The deformable barrier 4 is at least partially comprised of foam for desired resiliency and sound sealing properties. Sound from the exterior environment enters the ear plug through one or more exterior openings 12 in the exterior portion of the ear plug 14 (opposite the base end), passes through the interior chamber 8, to one or more sound openings 10 in the base end 2. When the ear plug is inserted in the ear of the user, the opening(s) in the base end 10 open into the ear canal of the user. In the embodiment shown in FIG. 1, the size of the deformable barrier 4 is selected so that in the open (undeformed) position, there is space between the outer circumference of the deformable barrier 4 and the inner circumference of the interior chamber 8. In this embodiment, the location of the sound opening 10 is such that in the open position there is at least one relatively unobstructed path for sounds to pass from the outside environment through the ear plug and into the ear of the user.

The exterior portion 14 of the ear plug, with exterior openings 12, may be a resilient foam, but may also be solid and made of various other, more rigid, materials since it is not critical that this portion form a tight seal with the ear canal. It is desirable, however, that the portions with openings contacted by the deformable barrier be sufficiently flexible to afford sealing of the openings and provide suitable sound attenuation. The base end 2 of the ear plug must seal well against the ear canal and should be a properly resilient material.

Figure 2:
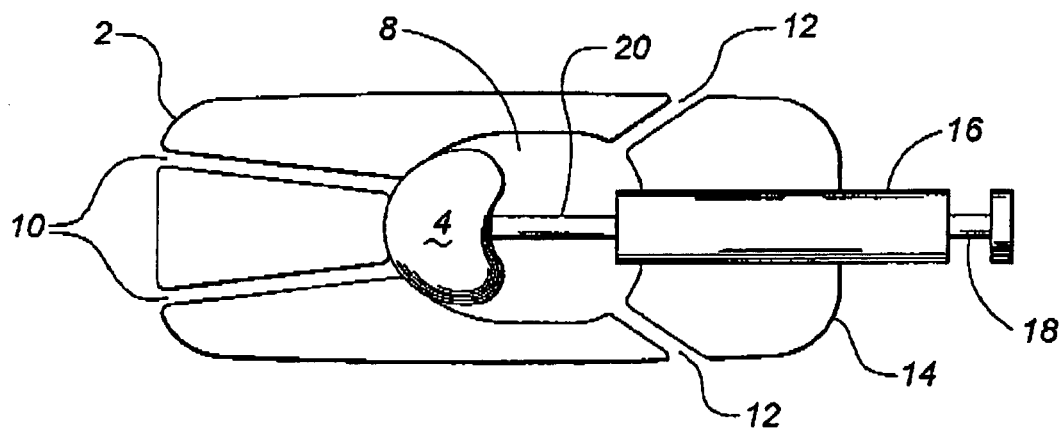
FIG. 2 shows a preferred embodiment of the hearing protection ear plug in the closed position in which substantial hearing protection and sound attenuation is provided.

As shown in FIG. 2, in the closed position, the deformable barrier 4 is compressed to form a tight seal between its outer circumference and the inner wall of the interior chamber 8, or at least is sufficiently compressed to block openings 10 and/or 12 to block sound passage through the ear plug. The placement of the sound openings 10 and 12 and the deformable barrier configuration would be a matter of choice to one skilled in the art. The deformable barrier 4 could be of various shapes that accomplish the same objectives. Preferably, however, the deformable barrier 4 and the interior chamber 8 would be essentially spherical and cylindrical, respectively.

FIGS. 1 and 2 show a deforming actuator 16 that presses against the deformable barrier 4 to cause its deformation. The deformable actuator 16 shown in FIGS. 1 and 2 can be similar to the mechanism in U.S. Pat. No. 7,182,087. When the exterior end 18 of the actuator is pressed, the interior piston 20 of the deforming actuator moves further into the interior chamber and deforms the deformable barrier 4 so that it blocks opening 10. The internal components of such an actuator are similar to those described in U.S. Pat. No. 7,182,087 and would be known to one skilled in the art. Switching based on pressure applied against the exterior end of the ear plug (pressing the ear plug in the direction of the ear of the user and thereby causing the ear plug to remain in place in the ear) is preferable over a switching force that tends to pull the ear plug out of the ear. In an alternative embodiment, various means available to one skilled in the art could be used to reduce the volume of the interior chamber and thereby cause suitable deformation of the deformable barrier.

In a preferred embodiment, the exterior portion 14 and base end 10 of the ear plug would be substantially integrated with an integral flexible foam portion between them defining the interior chamber, so that from the outside the ear plug would appear to be a uniform ear plug much like the typical one piece foam ear plugs. Other, less uniform, approaches would also be acceptable.

Proper sizing of the deformable barrier 4 is critical. Given the small desired size for the ear plug ear plug, the ideal spherical deformable barrier would ideally have an uncompressed diameter of between about ⅛ and ⅜ of an inch. The deformable barrier may be solid foam or a solid foam filled with a fluid. The material used for the deformable barrier (or its filling) may be selected from a range of foam, rubber and polymer products that have suitable properties of rebound resilience and durometer hardness. The deformable barrier should properly seal the sound opening(s).

Figure 3:
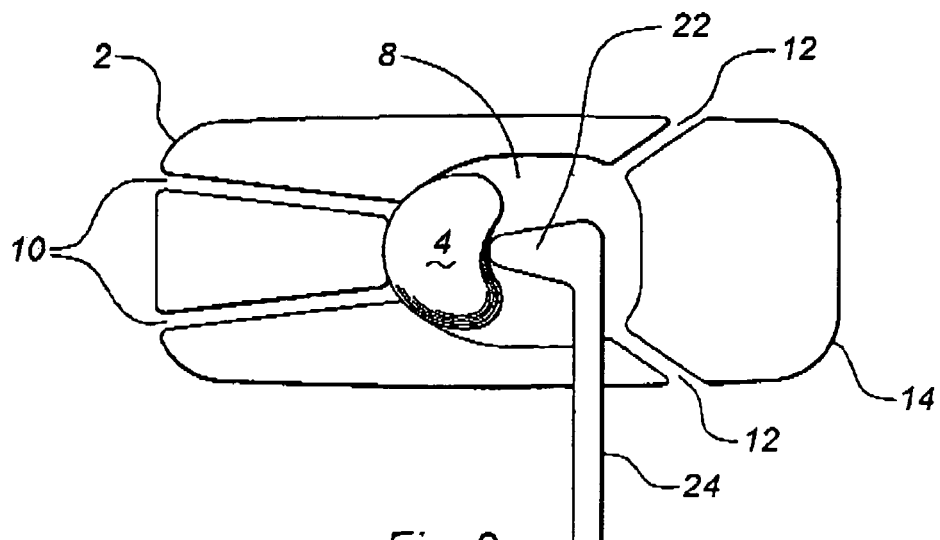
FIG. 3 shows an embodiment of the hearing protection ear plug with an alternative deforming actuator.

Other mechanisms for switching the ear plug between the open and closed positions may be used. FIG. 3 shows a deforming actuator that utilizes a moveable cam 22. In the closed position the cam 22 deforms the deformable barrier 4 and blocks the passage of sound through openings 10. Movement of the cam lever 24 would be based on force either in the direction of the ear or at least perpendicular to that direction so that lever movement should not tend to pull the ear plug out of the ear. A biasing force within the ear plug may be desirable to move the deforming actuator into a second position (either open or closed) so that a user-applied force away from the ear would not be needed. That biasing force may also be exerted by the deformable barrier as a result of its compression, as in the case of the actuator shown in FIG. 3. In such a configuration, it is desirable to use the deformable barrier as both the biasing means and as the means for blocking sound passage.

The number of sound openings in the base end 10 and the number of openings in the exterior portion 12, and their locations, are matters of choice to one skilled in the art. A suitable configuration would however, require blocking of all openings in either the base end or the exterior portion to block sound transmission in the closed position.

Other desirable approaches to switching between ear plug positions would include opening and closing with a twisting motion. Such a twisting closure could involve, for example, rotating a threaded exterior ear plug portion or twisting the exterior end to engage a locking tab to lock the ear plug either open or closed against a biasing force. Still other switching approaches would be easily utilized by one skilled in the art.

While the embodiments shown are in the closed position when the deformable barrier is substantially deformed and open when the deformable barrier is substantially undeformed, alternative opposite configurations would also be possible. In the opposite configuration sounds are blocked when the deformable barrier is in the substantially undeformed state, and sounds are transmitted when the deformable barrier is substantially deformed (and at least one each of openings 10 and openings 12 are unobstructed). In such an opposite configuration the openings 10 into the base end could be located nearer the exterior end 14 of the ear plug so that they would be blocked by a substantially undeformed deformable barrier, and not blocked when the deformable barrier is deformed by force in the direction of the base end 2.

I claim:

1. A hearing protection ear plug comprising:
    a base end, a portion of which is adapted to fit in the ear of a user,
    an interior chamber,
    at least one opening passing through the base end into the interior chamber,
    at least one opening passing from the interior chamber to an exterior of the ear plug,
    and a substantially spherical deformable barrier within the interior chamber wherein when said deformable barrier is in a substantially deformed state sound does not pass from said at least one opening passing through the base end into the interior chamber through the interior chamber to the said at least one opening passing from the interior chamber to an exterior of the ear plug, and when said deformable bather is in a less deformed or undeformed state, sound passes from said at least one opening passing through the base end into the interior chamber through the interior chamber to the said at least one opening passing from the interior chamber to an exterior of the ear plug.

2. The ear plug of claim 1 wherein said interior chamber is substantially cylindrical.

3. The ear plug of claim 1 further comprising a deforming actuator that in one of at least two positions deforms the deformable barrier and in another position does not deform the deformable barrier or deforms it to a lesser extent.

4. The ear plug of claim 3 wherein said deforming actuator is activated by force exerted in the direction of the base end of the ear plug.

5. The ear plug of claim 3 wherein said deforming actuator is activated with a rotational force.

6. The ear plug of claim 3 wherein said deforming actuator comprises an interior piston that moves into the interior chamber and deforms the deformable barrier.

7. The ear plug of claim 3 wherein the deformable barrier provides a biasing force to the deforming actuator.

8. A hearing protection ear plug comprising:
    a base end, a portion of which is adapted to fit in the ear of a user,
    an interior chamber,
    at least one opening passing through the base end into the interior chamber,
    at least one opening passing from the interior chamber to an exterior of the ear plug, a substantially spherical deformable barrier within the interior chamber, a deforming actuator that in one of at least two positions deforms the deformable bather and in another position does not deform the deformable barrier or deforms it to a lesser extent, wherein said deforming actuator comprises an interior piston that moves into the interior chamber and deforms the deformable barrier.

\* \* \* \* \*